(12) United States Patent
Wu et al.

(10) Patent No.: US 11,659,862 B2
(45) Date of Patent: May 30, 2023

(54) ELECTRONIC CIGARETTE

(71) Applicant: Shenzhen First Union Technology Co., Ltd., Shenzhen (CN)

(72) Inventors: Yifei Wu, Shenzhen (CN); Yonglu Guo, Shenzhen (CN); Zhongli Xu, Shenzhen (CN); Yonghai Li, Shenzhen (CN)

(73) Assignee: Shenzhen First Union Technology Co., Ltd., Shenzhen (CN)

( * ) Notice: Subject to any disclaimer, the term of this patent is extended or adjusted under 35 U.S.C. 154(b) by 1001 days.

(21) Appl. No.: 16/455,802

(22) Filed: Jun. 28, 2019

(65) Prior Publication Data

US 2020/0000147 A1     Jan. 2, 2020

(30) Foreign Application Priority Data

Jun. 29, 2018   (CN) .......................... 201821030086.2

(51) Int. Cl.
| | |
|---|---|
| *A24F 40/10* | (2020.01) |
| *A24F 40/40* | (2020.01) |
| *A61M 15/06* | (2006.01) |
| *A61M 11/04* | (2006.01) |

(52) U.S. Cl.
CPC .............. *A24F 40/40* (2020.01); *A24F 40/10* (2020.01); *A61M 11/042* (2014.02); *A61M 15/06* (2013.01)

(58) Field of Classification Search
CPC .......... A24F 40/00; A24F 40/10; A24F 40/20; A24F 40/30; A24F 40/40; A24F 40/42; A61M 11/042; A61M 15/06; A61M 15/026
See application file for complete search history.

(56) References Cited

U.S. PATENT DOCUMENTS

| | | | | |
|---|---|---|---|---|
| 2,159,698 A | * | 5/1939 | Harris ........................ | A24F 1/00 131/225 |
| 2,475,472 A | * | 7/1949 | Brown ....................... | A24F 1/00 131/225 |
| 2,601,857 A | * | 7/1952 | Smith ........................ | A24F 1/00 131/225 |
| 2,660,179 A | * | 11/1953 | Smith ........................ | A24F 1/00 131/225 |
| 9,877,520 B2 | * | 1/2018 | Rastogi ...................... | E05C 1/08 |
| 9,907,930 B2 | * | 3/2018 | Trzecieski ........... | A61M 11/042 |
| 10,448,456 B2 | * | 10/2019 | Shoched ................. | A24F 40/50 |

(Continued)

*Primary Examiner* — Alex B Efta
(74) *Attorney, Agent, or Firm* — PROI Intellectual Property US; Klaus Michael Schmid

(57) ABSTRACT

An electronic cigarette includes an atomizer with a first storage chamber formed in an end thereof, a first elastic element received in the first storage chamber, a first push pin slidably received in the first storage chamber. The first push pin is capable of sliding along an axial direction of the first storage chamber; an end of the first push pin abuts against the first elastic element. The electronic cigarette further comprises a power source assembly with a second storage chamber formed in an end thereof that is closer to the atomizer, a second elastic element received in the second storage chamber, a second push pin slidably received in the second storage chamber; the second push pin is capable of sliding along an axial direction of the second storage chamber; an end of the second push pin abuts against the second elastic element.

14 Claims, 17 Drawing Sheets

(56) References Cited

U.S. PATENT DOCUMENTS

| | | |
|---|---|---|
| 2013/0247910 A1 | 9/2013 | Postma |
| 2013/0248385 A1* | 9/2013 | Scatterday .............. A24F 15/01 |
| | | 206/86 |
| 2015/0164138 A1* | 6/2015 | Liu ..................... H01M 50/502 |
| | | 206/268 |
| 2017/0027228 A1 | 2/2017 | Rastogi |

* cited by examiner

ELECTRONIC CIGARETTE

CROSS REFERENCE TO RELATED APPLICATIONS

The present application claims priority to Chinese Patent Application CN201810700964.5 filed on Jun. 29, 2018 and Chinese Patent Application CN201821030086.2 filed on Jun. 29, 2018, which are hereby incorporated by reference herein as if set forth in its entirety.

TECHNICAL FIELD

The present disclosure relates to the field of cigarette articles, and particularly, to an electronic cigarette.

BACKGROUND ART

An electronic cigarette as an electronic product mimicking traditional cigarettes has a same aerosol, taste and feeling of smoking. By relying on vaporization of a tobacco liquid solution, typically a heating element atomizes the tobacco liquid solution, the tobacco liquid solution containing nicotine etc. becomes an aerosol inhaled by the user. Since the electronic cigarette is portable, immune from open flames and environmental friendly, the electronic cigarette attracts an abundance of smokers.

The electronic cigarette typically includes an atomizer and a power source. The atomizer heats the tobacco liquid solution upon powered on, to generate an aerosol for users to inhale. The power source is configured for supplying power to the atomizer.

During the invention process, the inventors are aware of the prior art power sources and atomizers which integrate with each other, the electronic cigarette has a comparatively long length, therefore it is not convenient to carry or use.

SUMMARY

To overcome the above drawbacks, the present disclosure generally relates to a foldable electronic cigarette which may reduce the length of the electronic cigarette, and make the electronic cigarette convenient to carry or use.

According to embodiments of the present disclosure, an electronic cigarette is disclosed including:

an atomizer, with a first storage chamber formed in an end thereof;

a first elastic element, received in the first storage chamber;

a first push pin, slidably received in the first storage chamber; the first push pin capable of sliding along an axial direction of the first storage chamber; an end of the first push pin abutting against the first elastic element;

a power source assembly, with a second storage chamber formed in an end thereof that is closer to the atomizer;

a second elastic element, received in the second storage chamber;

a second push pin, slidably received in the second storage chamber; the second push pin capable of sliding along an axial direction of the second storage chamber; an end of the second push pin abutting against the second elastic element; and a connector, an end thereof pivotally connected to the atomizer; an opposite end thereof pivotally connected to the power source assembly;

wherein, the opposite end of the first push pin abutting against the connector;

the opposite end of the second push pin abutting against the connector; when the atomizer or the power source assembly rotating round the connector, the first push pin capable of sliding along a surface of the connector and the second push pin capable of sliding along another surface of the connector.

As used herein, the connector including a connecting body, at least one first connecting axle and at least one second connecting axle; the first connecting axle and the second connecting axle parallel with each other, spaced apart and secured to the connecting body;

two opposite sides of the first storage chamber bored with first pivot holes; two opposite sides of the second storage chamber bored with second pivot holes; the first connecting axle passing through the first pivot holes; the second connecting axle passing through the second pivot holes; the opposite end of the first push pin abutting against the connector; the opposite end of the second push pin abutting against the connector.

The electronic cigarette further including:

a first protruding pillar carried on the atomizer;

a second protruding pillar carried on the power source assembly;

a first drag spring, one end thereof secured to the first protruding pillar, an opposite end thereof secured to the first connecting axle;

a second drag spring, one end thereof secured to the second protruding pillar, an opposite end thereof secured to the second connecting axle;

when the atomizer being rotating around the connector, the second drag spring supplying a second elastic force for preventing the atomizer from rotating around the connector; when the power source assembly being rotating around the connector, the first drag spring supplying a first elastic force for preventing the power source assembly from rotating around the connector.

The electronic cigarette further including:

two first protruding pillars, respectively carried on two sides of the atomizer;

two first drag springs, respectively carried on two sides of the atomizer;

two second protruding pillars, respectively carried on two sides of the power source assembly;

two second drag springs, respectively carried on two sides of the power source assembly.

As used herein, the atomizer having a first axis, the power source assembly having a second axis;

when the first axis being coaxial with the second axis, the first drag spring and the second drag spring in an initial state;

when the first axis being perpendicular to the second axis, the first drag spring and the second drag spring in an initial state;

when the first axis being parallel with the second axis, the first drag spring and the second drag spring in an initial state;

As used herein, the connecting body including a first surface and a second surface opposite with each other, a third surface and a fourth surface opposite with each other, a fifth surface and a sixth surface opposite with each other; the atomizer having a first axis, the power source assembly having a second axis;

when the first axis is coaxial with the second axis, the opposite end of the first push pin abutting against the first surface, and the opposite end of the second push pin abutting against the third surface;

when the first axis is perpendicular to the second axis, the opposite end of the first push pin abutting against the fourth surface, and the opposite end of the second push pin abutting against the third surface;

when the first axis is parallel with the second axis, the opposite end of the first push pin abutting against the fourth surface, and the opposite end of the second push pin abutting against the second surface.

As used herein, the first push pin having a first base, a first extending part extending from an side of the first base; a first pushing part extending from an opposite side of the first base; the first elastic element partially received in the first extending part to abut against the first base; the first pushing part abutting against the connector;

the second push pin having a second base, a second extending part extending from an side of the second base; a second pushing part extending from an opposite side of the second base; the second elastic element partially received in the second extending part to abut against the second base; the second pushing part abutting against the connector;

As used herein, the first surface having a first plane, the second surface having a second plane, the third surface having a third plane, the fourth surface having a fourth plane, the first plane parallel with the second plane, the third plane parallel with the fourth plane; the third plane perpendicular to the first plane;

the first pushing part having a flat distal end with respect to the first base; the second pushing part having a flat distal end with respect to the second base;

when the first axis and the second axis coaxial with each other, the first pushing part abutting against the first plane, and the second push part abutting against the third plane;

when the first axis perpendicular to the second axis, the first pushing part abutting against the fourth plane, the second pushing part abutting against the third plane;

when the first axis parallel with the second axis, the first pushing part abutting against the fourth plane, the second pushing part abutting against the second plane.

The electronic cigarette further including a first magnetic element and second magnetic element, the first magnetic element secured to the atomizer, the second magnetic element secured to the power source assembly;

when the first axis is coaxial with the second axis, the first magnetic element right facing the second magnetic element, and opposite sides of the first magnetic element and the second magnetic element having different magnetic polarities.

The electronic cigarette further including a third magnetic element and a fourth magnetic element; the third magnetic element secured to the atomizer, the fourth magnetic element secured to the power source assembly;

when the first axis parallel with the second axis, the third magnetic element right facing the fourth magnetic element, and opposite sides of the third magnetic element and the fourth magnetic element having different magnetic polarities.

As used herein, an intersection between the first plane and the fourth plane being an arc surface, and an intersection between the second plane and the third plane being an arc surface.

The first push pin having a third axis, the second push pin having a fourth axis, the third axis parallel with the first axis, the fourth axis perpendicular to the second axis.

The electronic cigarette further including two first connecting axles coaxial with each other;

an end of one first connecting axle passing through the fifth surface to be secured on the connecting body; an end of the other one first connecting axle passing through the sixth surface to be secured on the connecting body; opposite ends of the two first connecting axles respectively passing through the first pivot holes to be secured on the power source assembly;

two second connecting axles coaxial with each other; an end of one second connecting axle passing through the fifth surface to be secured on the connecting body; an end of the other one first connecting axle passing through the sixth surface to be secured on the connecting body; opposite ends of the two second connecting axles respectively passing through the second pivot holes to be secured on the power source assembly.

The electronic cigarette further including:

two first electrodes, made by electrically conductive materials; the two first electrodes respectively sleeved on the two first connecting axles, each first connecting axle rotatable around the corresponding first electrode; wherein, the two first connecting axles made by electrically conductive materials and not to contact with each other;

two second electrodes, made by electrically conductive materials; the two second electrodes respectively sleeved on the two second connecting axles, each second connecting axle rotatable around the corresponding second electrode; wherein the two second connecting axles made by electrically conductive materials and not to contact with each other;

two transmission parts made by electrically conductive materials; the two transmission parts respectively located on the fifth plane and the sixth plane of the connecting body; one of the transmission parts at the fifth plane, electrically coupled with the first connecting axle and the second connecting axle; the other one of the transmission parts at the sixth plane, electrically coupled with the first connecting axle and the second connecting axle;

the atomizer having a first positive contact pole and first negative pole; the first positive contact pole contacting one of the two first electrodes; the first negative pole contacting the other one of the two first electrodes; the power source assembly having a second positive pole and a second negative pole; the second positive pole contacting one of the two second electrodes, the second negative pole contacting the other one of the two second electrodes; the first positive pole electrically coupled with the second positive pole, the first negative pole electrically coupled with the second negative pole, enabling the power source assembly being electrically coupled with the atomizer.

Compared to the prior art, the connector of the electronic cigarette in the present disclosure has one end pivotally connected to the atomizer, the opposite end thereof is pivotally connected to the power source assembly, which enables the atomizer and the power source assembly to rotate around the connector, therefore making the electronic cigarette foldable and reducing a length of the electronic cigarette, easy to carry or use. On the other hand, by means of the first push pin and the second push pin abutting against the connector bring a better rotating experience when the user is rotating the atomizer or the power source assembly. Meanwhile, by means of the first push pin and the second push pin abutting against the connector exert abutting forces to the atomizer and the power source assembly, so as to make the atomizer and the power source assembly stable in a certain angle.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

NUMERALS INDICATING COMPONENTS ARE ILLUSTRATED HEREIN

Figure 1:
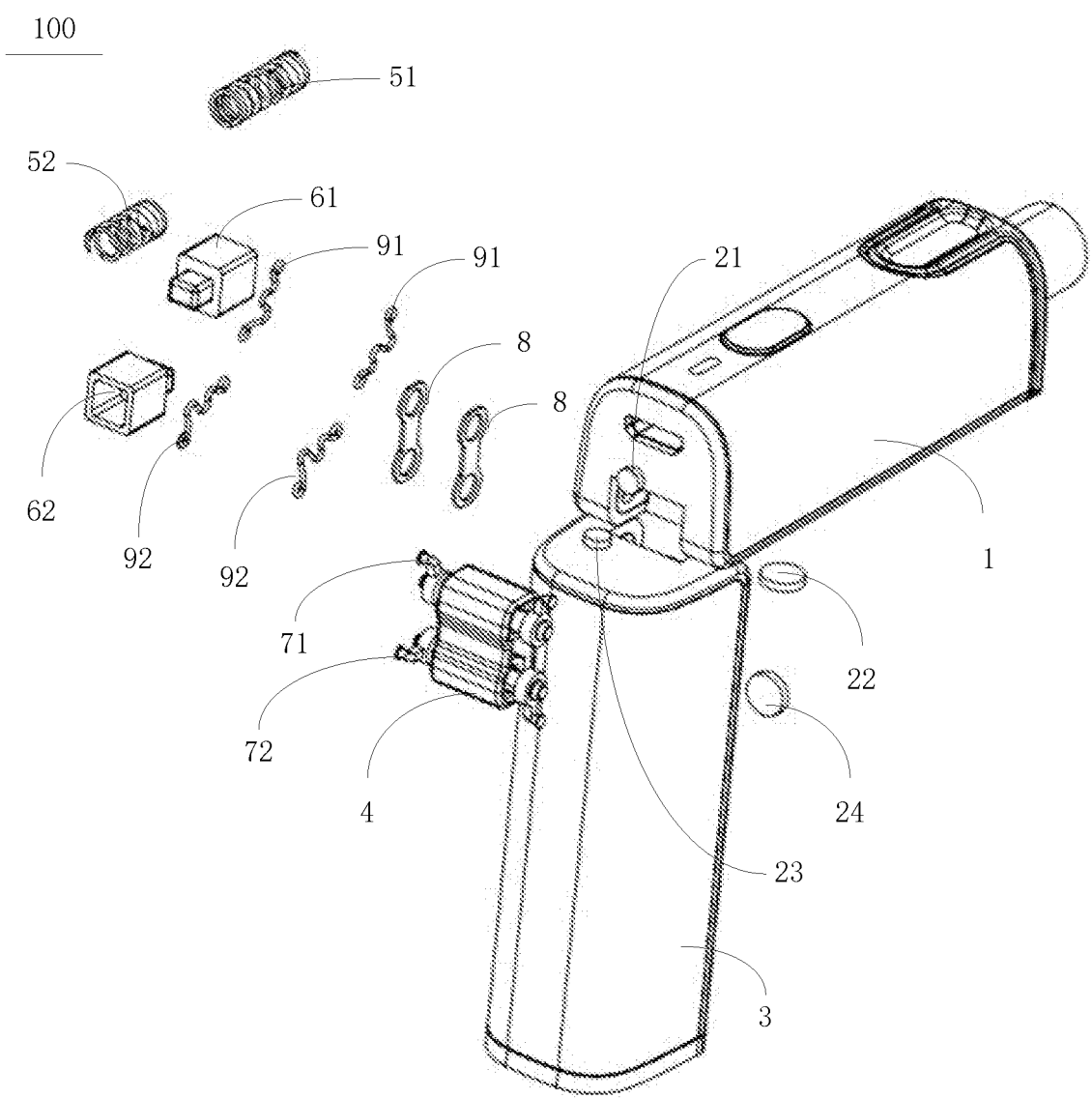
FIG. 1 is an exploded view of an electronic cigarette according to an embodiment of the present disclosure.

| | | | |
|---|---|---|---|
| Electronic cigarette 100 | Atomizer 1 | Atomizing shell 11 | First shell 111 |
| Fixing hole 1111 | Second shell 112 | First substrate plate 1121 | Interface 1122 |
| First plate 1123 | First sheet 1124 | Second sheet 1125 | Cover 12 |
| First body 121 | First pivot plate 122 | First pivot hole 123 | First storage chamber 13 |
| First bump 124 | Circuit board assembly 14 | Circuit board 141 | USB jack 142 |
| Button 15 | Reservoir 16 | Heater 17 | First magnet 21 |
| Second magnet 22 | Third magnetic element 23 | Fourth magnetic element 24 | Power source 3 |
| Power source shell 31 | Third shell 311 | Fourth shell 312 | Second substrate plate 3121 |
| Third sheet 3122 | Fourth sheet 3123 | Power source bezel 313 | Second body 3131 |
| Second pivot plate 3132 | Fifth sheet 3133 | Second pivot hole 3134 | Second protruding pillar 3135 |
| Second storage chamber 32 | Battery 33 | Second positive pole 34 | Second negative pole 35 |
| Connector 4 | Connecting body 41 | First surface 411 | First plane 4111 |
| Second surface 412 | Second plane 4121 | Third surface 413 | Third plane 4131 |
| Fourth surface 414 | Fourth plane 4141 | Fifth surface 415 | Sixth surface 416 |
| Second axis 30 | Second plate 3124 | First connecting axle 42 | Second connecting axle 43 |
| First elastic element 51 | Second elastic element 52 | First push pin 61 | First base 611 |
| First extending part 612 | First pushing part 613 | Third axis 614 | Second push pin 62 |
| Second base 621 | Second extending part 622 | Second pushing part 623 | Fourth axis 624 |
| First electrode 71 | Second electrode 72 | Transmission part 8 | First drag spring 91 |
| Second drag spring 92 | First axis 10 | | |

DETAILED DESCRIPTION

Provided herein are an electronic inhalable aerosol device (alternatively referred to as vaporization devices or electronic vaping devices etc.) generally heats a tobacco solution containing nicotine to generate an aerosol, eventually drawn by the users.

As shown in FIG. 1, the present disclosure provides an electronic cigarette 100 mainly includes an atomizer 1, a power source 3, a connector 4, a first elastic element 51, a first push pin 61, a second elastic element 52, a second push pin 62, a first drag spring 91, a second drag spring 92, a first magnet 21, a second magnet 22, a third magnet 23, a fourth magnet 24, a first electrode 71, a second electrode 72 and a transmission part 8.

Figure 2:
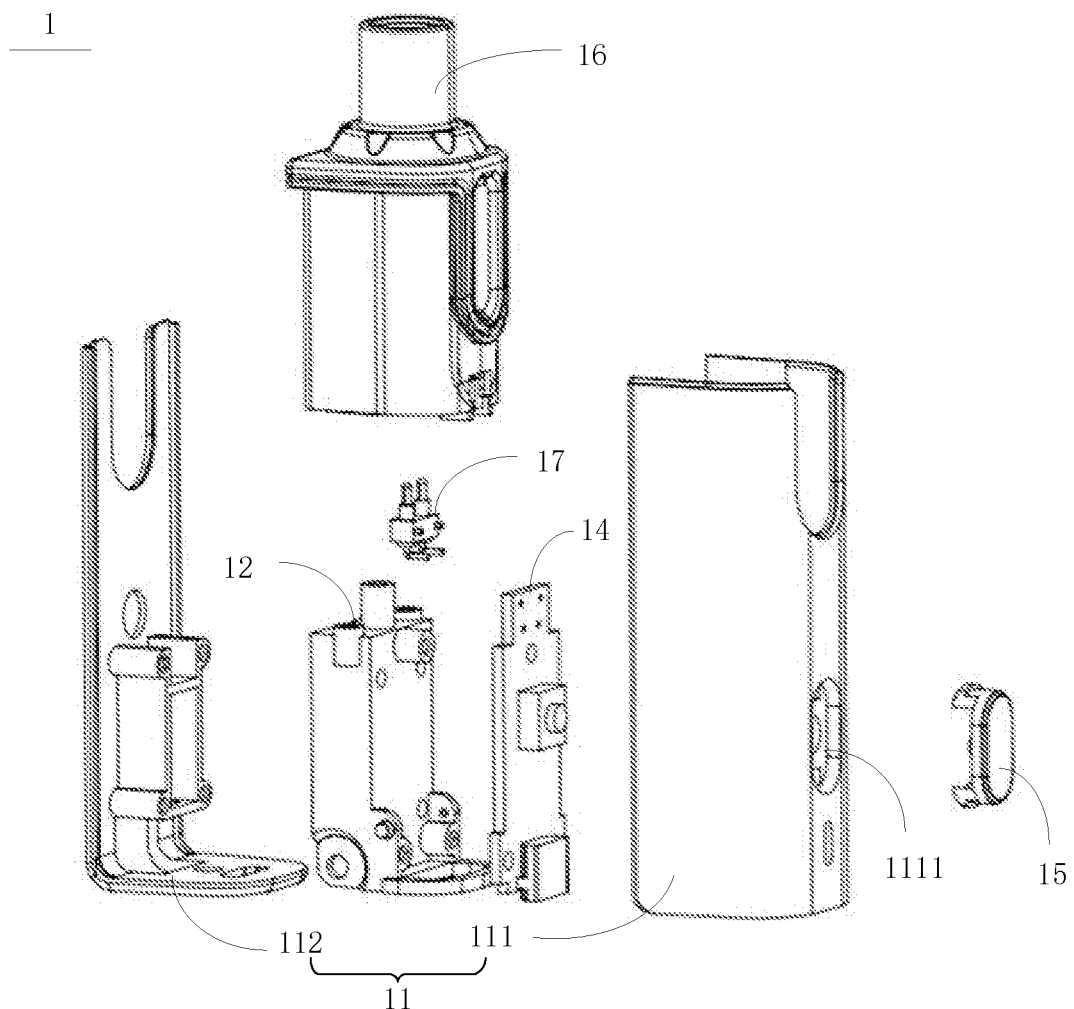
FIG. 2 is a structural isometric view of an atomizer in the electronic cigarette according to an embodiment of the present disclosure.

As shown in FIG. 2, the atomizer 1 includes an atomizing shell 11, a cover 12, a circuit board assembly 14, a button 15, a reservoir 16 and a heater 17.

As shown in FIG. 2, the atomizer shell 11 includes a first shell 111 and a second shell 112. The atomizer shell 11 has a distal end and a proximal end, and a mouthpiece is at the proximal end of the atomizer shell 11; the distal end and a proximal end defined a longitudinal direction of the electronic cigarette 100, a transverse direction is perpendicular to the longitudinal direction.

The first shell 111 is a structure opened on proximal, distal and lateral sides. The first shell 111 has a fixing hole 1111 for securing a button 15 to the first shell 111.

Figure 3:
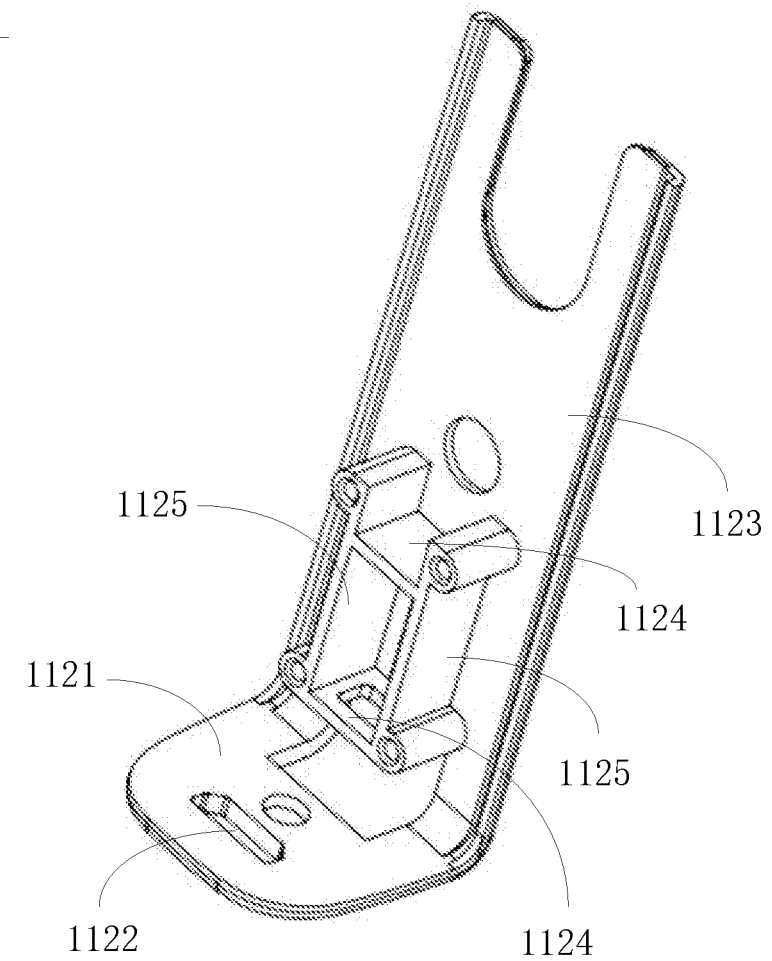
FIG. 3 is an isometric view of a second shell in the electronic cigarette according to an embodiment of the present disclosure.

Referring to FIG. 3, the second shell 112 has a roughly "L" shape, including a first substrate plate 1121 and a first plate 1123 that is perpendicular to the first substrate plate 1121. The first shell 111 and the second shell 112 encompasses the reservoir 16, the cover 12, the heater 17 and the circuit board assembly 14. An interface 1122 is bored on the first substrate plate 1121, through two opposite sides of the first substrate plate 1121.

Tow first sheets 1124 and two second sheets 1125 are extending from the first plate 1123 towards the second shell 112; the two first sheet 1124 are parallel with the first substrate plate 1121. One first sheet 1124 nearer to the first substrate plate 1121 is bored a centre hole (not shown) through two opposite sides of the particular first sheet 1124. Intersections of two first sheets 1124 and two second sheets 1125 have internal threads, that is, four internal threads. A middle of intersection of the first substrate plate 1121 and the first plate 1123 is bored a first receptacle notch (not shown).

Figure 4:
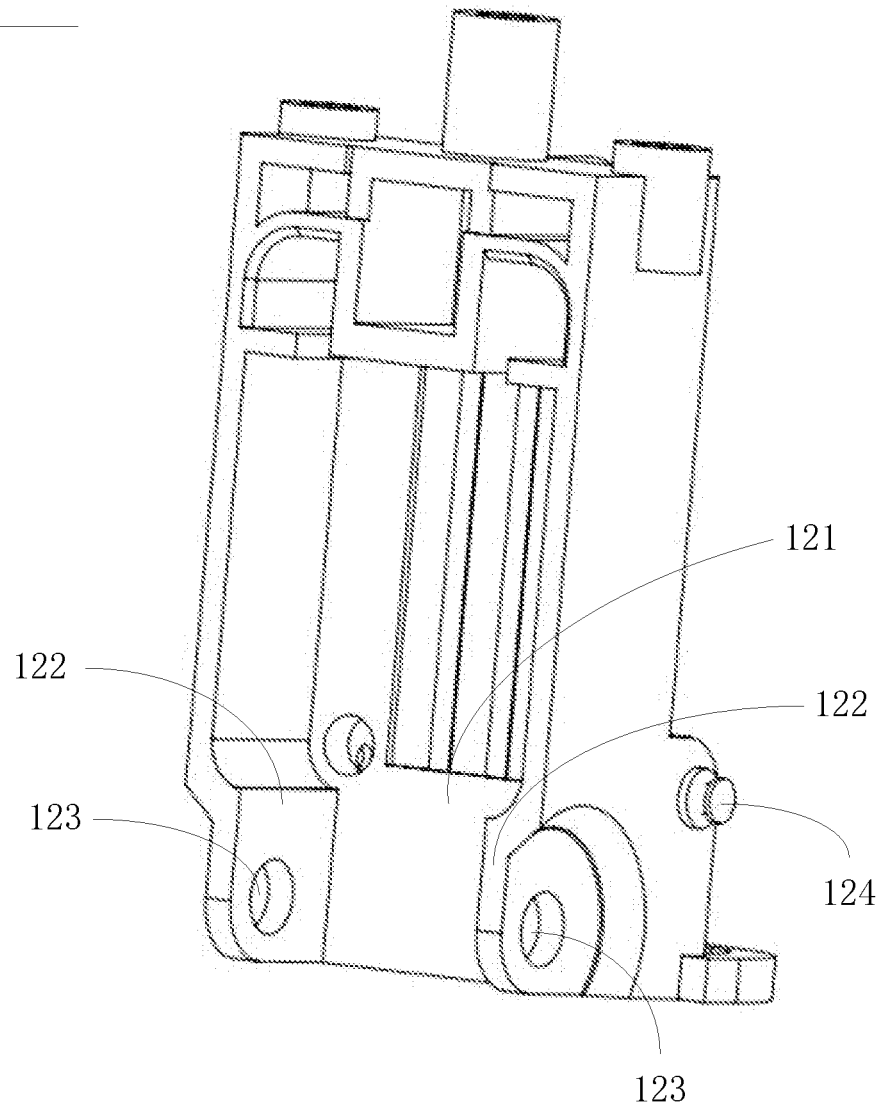
FIG. 4 is an isometric view of a cover in the electronic cigarette according to an embodiment of the present disclosure.

As shown in FIG. 4, the cover 12 includes a first body 121 that is parallel with the first plate 1123. Two first pivot plates 122 are extending from two opposite sides of the first body 121 towards the first plate 1123. A distal end of each first pivot plate 122 has a first pivot hole 123 through the first pivot plate 122. The first body 121 has a through hole (not shown) corresponding to the above internal thread. The cover 12 is secured to the first sheets 1124 and second sheets 1125, in this case, the first body 121, two first sheets 1124 and two second sheets 1125 define a first storage chamber 13. Since the two first pivot plates 122 are located outside the first storage chamber 13, the first pivot hole 123 is positioned outside the first storage chamber 13. The cover 12 may be secured to the first plate 1123 by a screw bolt passing through the through hole of the first body 121 to be engaged with the internal thread.

Two first protruding pillars 124 are respectively protruding on two opposite sides of two first pivot plates 122 along the transverse direction. Corresponding to the internal threads as described above, the first body 121 has internal threads along the transverse direction accordingly.

Understandable, in some embodiments, the first protruding pillars 124 are fixedly secured to the first pivot plates 122, in other words, the first protruding pillars 124 and the first pivot plates 122 are not integral with each other.

Figure 5:
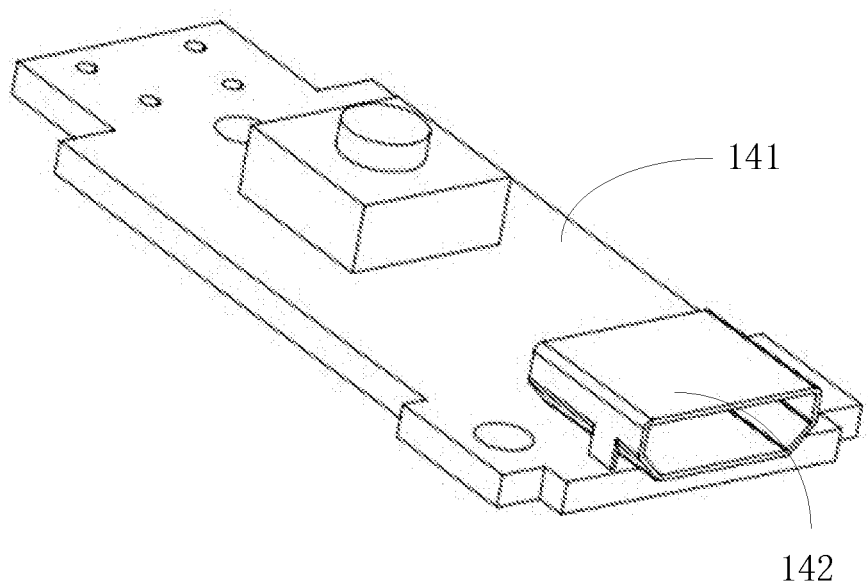
FIG. 5 is an isometric view of a circuit board assembly in the electronic cigarette according to an embodiment of the present disclosure.

Referring to FIG. 5, the circuit board assembly 14 includes a circuit board 141 and an universal serial bus jack 142 (abbreviated as "USB jack"). The circuit board 141 has through holes corresponding to the internal threads of the first body 121. The circuit board 141 may be secured to the cover 12 by the through holes thereof engaging with the internal threads of the first body 121. The circuit board 141 is provided with a charging circuit (not shown), a switch circuit (not shown), a first positive pole (not shown) and a first negative pole (not shown). The charging circuit is configured for making exterior currents stable for charging the electronic cigarette 100, avoiding overcharge for the electronic cigarette 100. The switch circuit is configured to control on/off of the atomizer 1, that means controlling electrical conduction or cutoff between the power source 3 and the atomizer 1.

The USB jack 142 is electrically conductive with the circuit board 141, and secured to the circuit board 141. The USB jack 142 faces with the interface 1122 on first substrate plate 1121.

The button 15 is secured in the fixing hole 1111 of the first shell 111, passing through the fixing hole 1111 to contact with the circuit board 141. The user may press the button 15 to control conduction or cutoff of the switch circuit on the circuit board 141, therefore control on/off of the atomizer 1.

Referring to FIG. 2, the reservoir 16 is secured on the first plate 1123, the reservoir 16 is disposed over the cover 12, configured to hold the tobacco liquid.

The heater 17 is electrically coupled with the circuit board 141. Upon the heater 17 is powered on, the heater 17 may heat the tobacco liquid in the reservoir 16, therefore the tobacco liquid is aerosolized for the user to draw.

The first magnetic element 21 and third magnetic element 23 are both permanent magnet. The first magnetic element 21 is secured on the first substrate plate 1121. The third magnetic element 23 is secured on the first plate 1123.

Since the atomizing shell 11 is elongate, the atomizing shell 11 has a first axis 10 extending along an axial direction of the atomizing shell 11.

Figure 6:
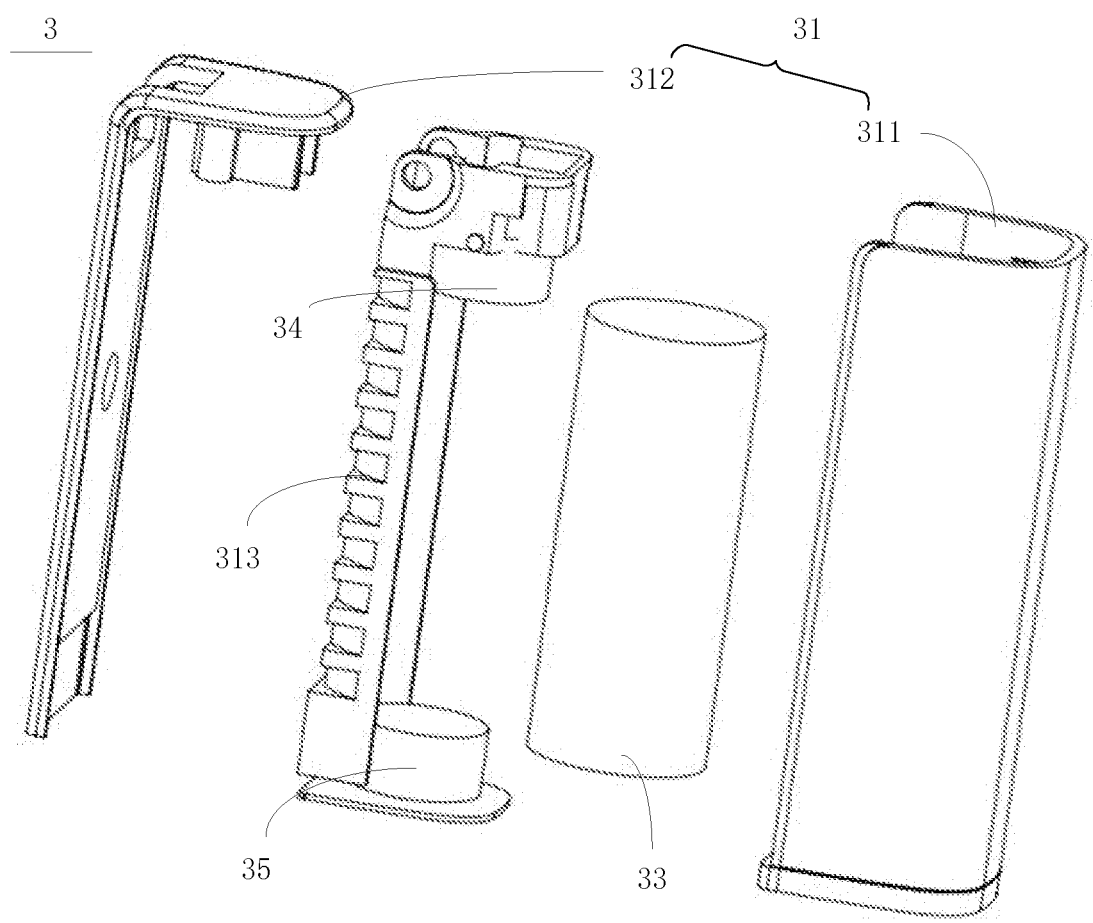
FIG. 6 is an exploded view of a power source in the electronic cigarette according to an embodiment of the present disclosure.

Referring to FIG. 6, the power source 3 includes a power source shell 31, a battery 33, a power source bezel 313, a second positive pole 34 and a second negative pole 35.

The power source shell 31 includes a third shell 311 and a fourth shell 312.

The third shell 311 has two adjacent sides opened, as shown in FIG. 6.

Figure 7:
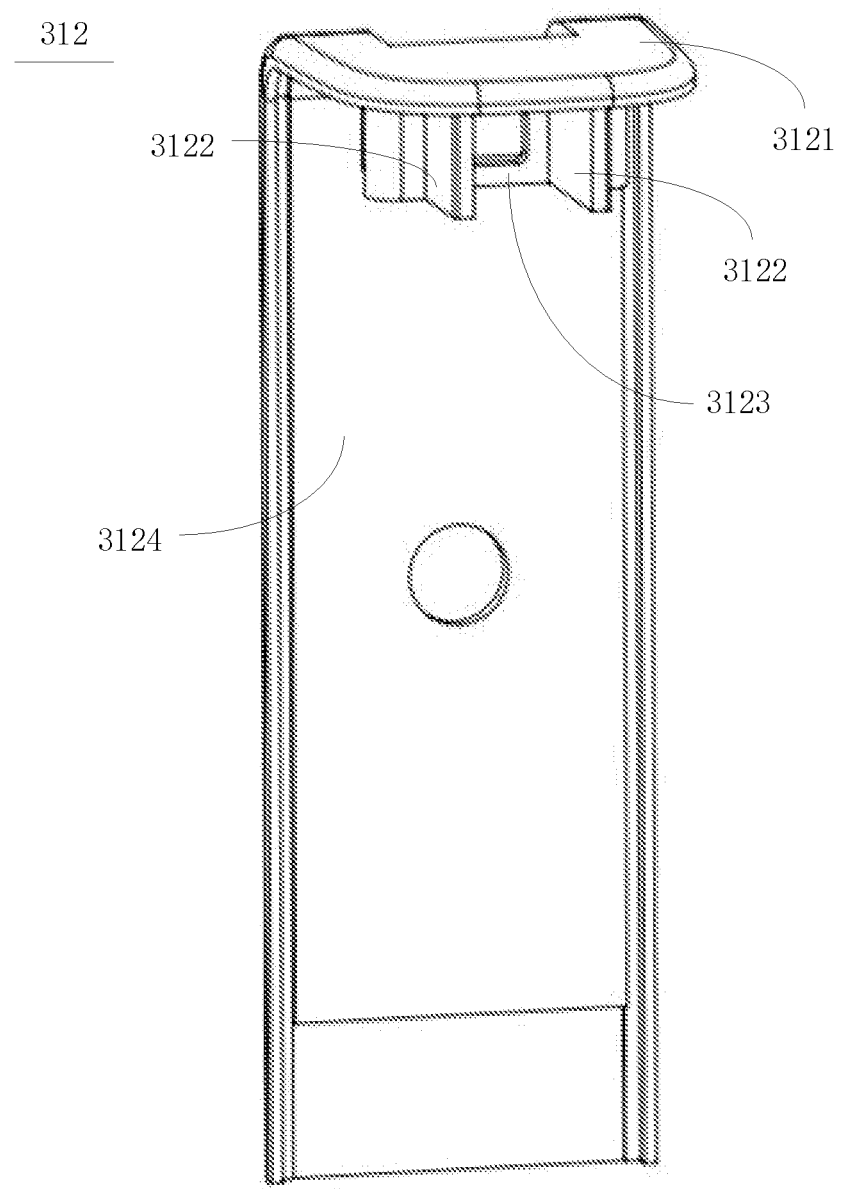
FIG. 7 is a structural isometric view of a fourth shell in the electronic cigarette according to an embodiment of the present disclosure.

Referring to FIG. 7, the fourth shell 312 includes a second substrate plate 3121 and a second plate 3124 that is perpendicular to the second substrate plate 3121. A middle of intersection of the second substrate plate 3121 is bored with a second receptacle notch (not shown).

Two third sheets 3122 and a fourth sheet 3123 that is connected with two third sheets 3122 are extending from the second substrate plate 3121. Two fixing poles (not shown) are carried on the second substrate plate 3121, with internal threads formed herein. Two fixing poles are respectively located adjacent to two outside surfaces of two third sheets 3122. The fourth sheet 3123 is parallel with the second plate 3124. A middle of the fourth sheet 3123 is bored with a through opening.

Figure 8:
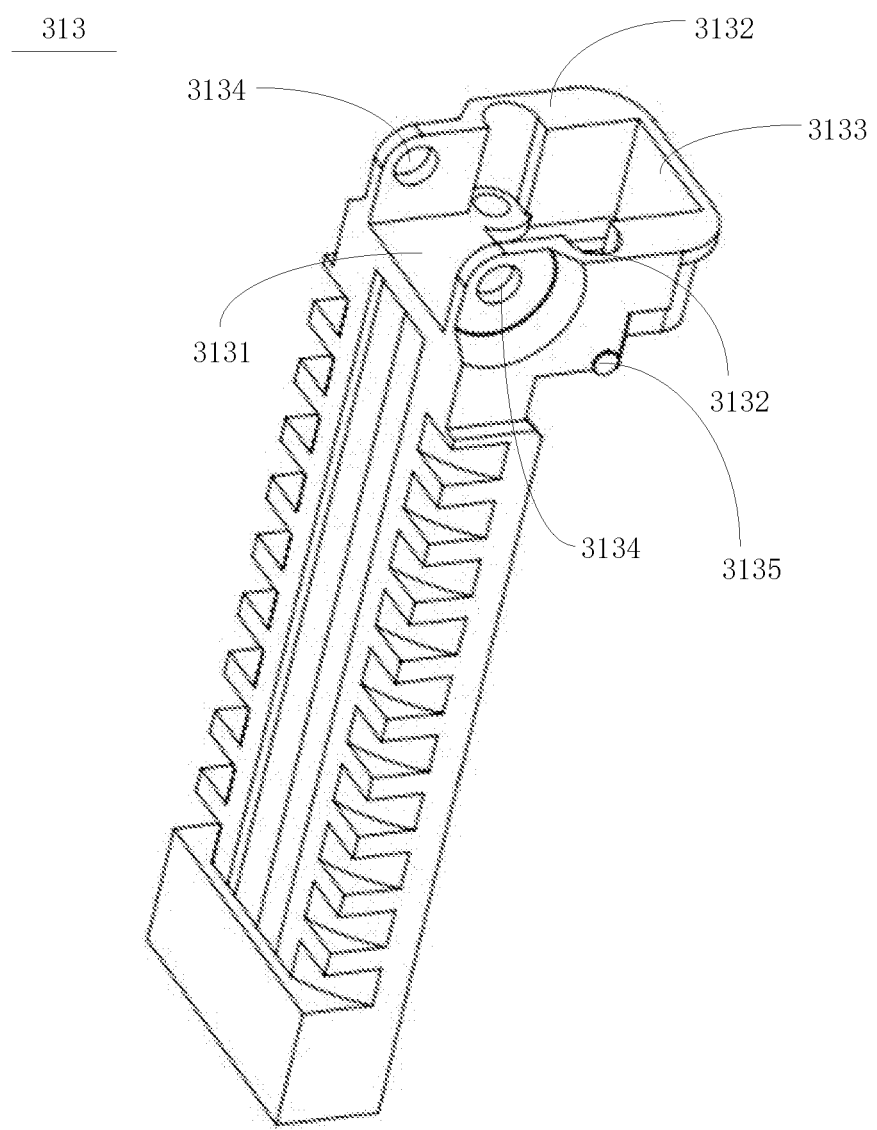
FIG. 8 is a structural isometric view of a supporter in the electronic cigarette according to an embodiment of the present disclosure.

Referring to FIG. 8, the power source bezel 313 has a second body 3131 that is perpendicular to the second substrate plate 3121. The second body 3131 is bored with two matching holes for securing two fixing poles, in this case, by means of a screw bolt passing through the matching holes of the second body 3131 to be engaged with the internal threads of the fixing poles, the power source bezel 313 is secured to the fourth shell 312.

Two second pivot plates 3132 and a fifth sheet 3133 there between are extending from two opposite side edges of the second body 3131 towards the second substrate plate 3121. The fifth sheet 3133 is parallel to the second plate 3124. The fourth sheet 3123 is located between the fifth sheet 3133 and the second plate 3124. An end of each second pivot plates 3132 distal to the fifth sheet 3133 is bored with a second pivot hole 3134. Each second pivot plates 3132 has a second protruding pillar 3135 formed thereon. The second body 3131, the fifth sheet 3133, the third sheet 3122 and the fourth sheet 3123 encompass a second storage chamber 32, as described herein, the second pivot sheet 3132 are respectively located outside two third sheet 3122.

Understandable, in some embodiments, the second protruding pillar 3135 is assembled on the second pivot sheet 3132, that means, the second protruding pillar 3135 and the second pivot sheet 3132 is not integral.

The battery 33 may be a rechargeable battery 33 secured to the power source bezel 313. Two ends of the battery 33 respectively have a second positive pole 34 and a second negative pole 35. A power source shell 31 encompassed by the third shell 311 and fourth shell 312 is configured to hold the battery 33.

Due to the elongate power source shell 31, the power source assembly 3 has a second axis 30 that is the same as an axis of the power source shell 31.

A third magnetic element 23 is secured to the second substrate plate 3121; the fourth magnetic element 24 is secured to the second plate 3124.

Figure 9:
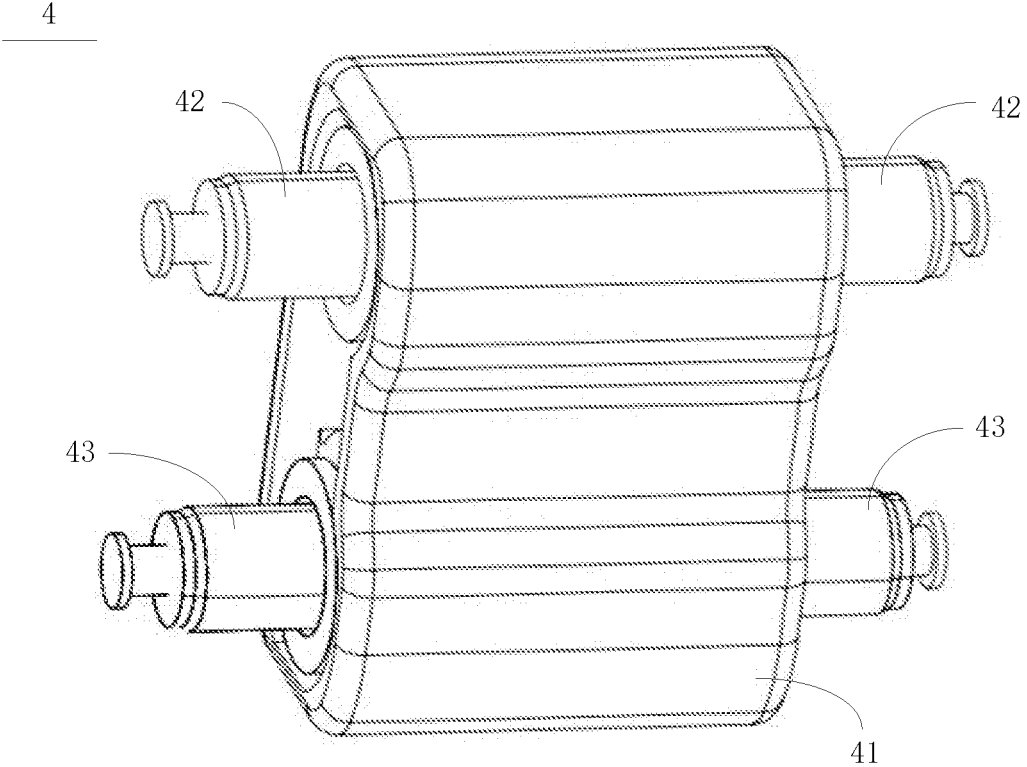
FIG. 9 is an isometric view of a connector in the electronic cigarette according to an embodiment of the present disclosure.
Figure 10:
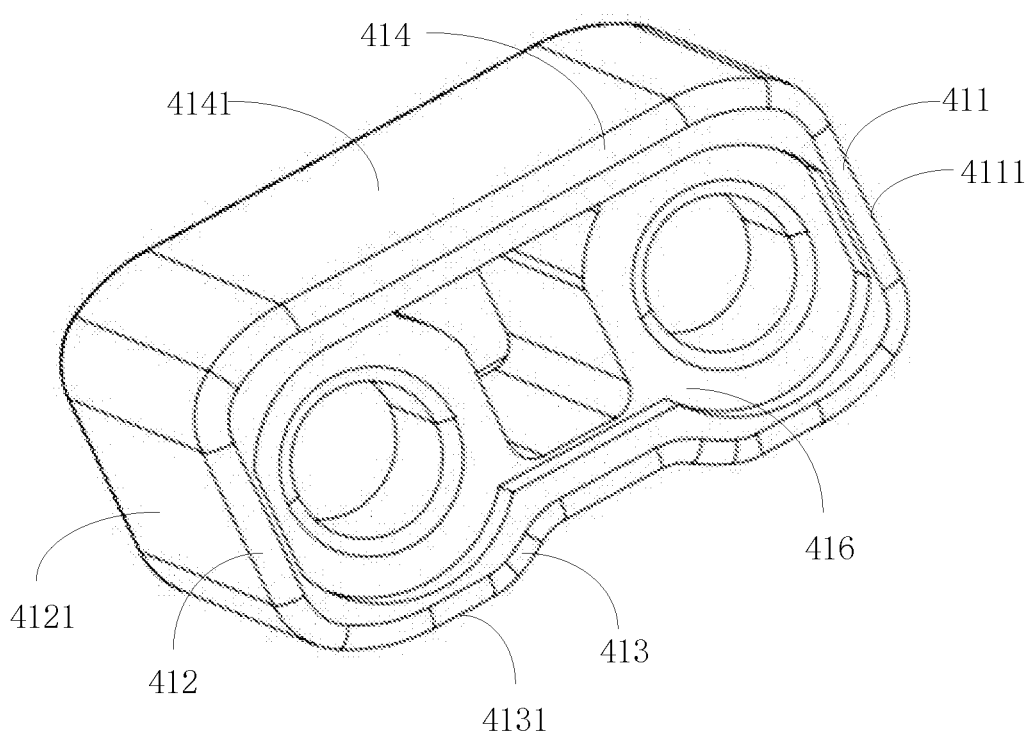
FIG. 10 is an isometric view of a connecting body in the electronic cigarette according to an embodiment of the present disclosure.

Referring to FIGS. 9 and 10, a connecting body 41 has a first surface 411 and a second surface 412 opposite with each other, a third surface 413 and a fourth surface 414 opposite with each other, a fifth surface 415 and a sixth surface 416 opposite with each other. The first surface 411 has a first plane 4111, the second surface 412 has a second plane 4121, the third surface 413 has a third plane 4131, the fourth surface 414 has a fourth plane 4141, as described herein, the first plane 4111 is parallel with the second plane 4121; the third plane 4131 is parallel with the fourth plane 4141; the third plane 4131 is perpendicular to the first plane 4111. The intersection between the first plane 4111 and the fourth plane 4141 is an arc surface; the intersection between the second plane 4121 and the third plane 4131 is an arc surface.

The first plane 4111 is received in the first receptacle notch, the second plane 412 is received in the second receptacle notch.

The two first connecting axles 42 are coaxial without touching each other, the first connecting axles 42 are made by electrically conductive materials. Each first connecting axle 42 is secured to the connecting body 41 via an end thereof inserted through the fifth surface 415 or the sixth surface 416. The opposite end of each first connecting axle 42 is inserted through one first pivot hole 123 for being secured to the atomizer 1. An outer diameter of the first connecting axle 42 is less than an inner diameter of the first pivot hole 123.

Two second connecting axles 43 are provided herein and coaxial with each other, each second connecting axle 43 is secured to the connecting body 41 via an end thereof inserted through the fifth surface 415 and the sixth surface 416. The opposite end of each second connecting axle 43 is inserted through the second pivot hole 3134 for being secured to the power source assembly 3. The second connecting axles 43 are parallel with the first connecting axles 42, spaced apart and secured to the connecting body 41. An outer diameter of the second connecting axle 43 is less than an inner diameter of the second pivot hole 3134.

The first elastic element 51 is received in the first storage chamber 13, as described herein, the first elastic element 51 is a compressible spring.

Figure 11:
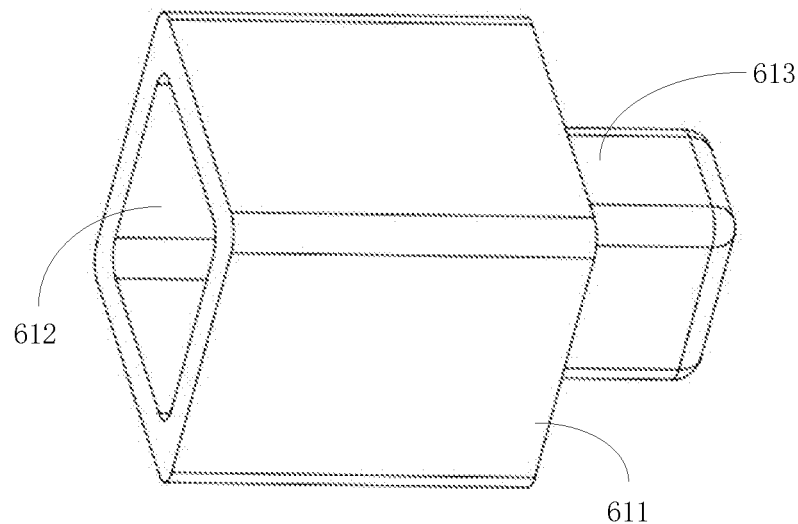
FIG. 11 is an isometric view of a first push pin in the electronic cigarette according to an embodiment of the present disclosure.

Referring to FIG. 11, the first push pin 61 includes a first base 611 that is parallel with the first sheet 1124, a first extending part 612 is extending from one side of the first base 611, a first pushing part 613 is extending from the opposite side of the first base 611. With respect to the first base 611, a distal end of the pushing part 613 is a flat plane. The first push pin 61 has a third axis 614 that is parallel with the first axis 10.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

The extending part 612 is received in the first storage chamber 13. The first elastic element 51 is partially received in the extending part 612, one end of the elastic element 51 abuts against the first sheet 1124; the opposite end thereof abuts against the first base 611. The pushing part 613 passes through the opening of the first sheet 1124 (i.e. outside the first storage chamber 13) to abut against the connecting body 41, that means an end of the push pin 61 (the first base 611) abuts against the first elastic element 51 to compress the first elastic element 51, the opposite end of the push pin 61 (the first pushing part 613) abuts against the connector 4 (the connecting body 41). The first push pin 61 (the first extending part 612) is received in the first storage chamber 13 and sliding along an axial direction of the storage chamber 13.

Understandable, in some embodiments, the first elastic element 51 and the first push pin 61 may be connected via bezel setting.

The second elastic element 52 is received in the second storage chamber 32, the second storage chamber 52 is compressible spring.

Figure 12:
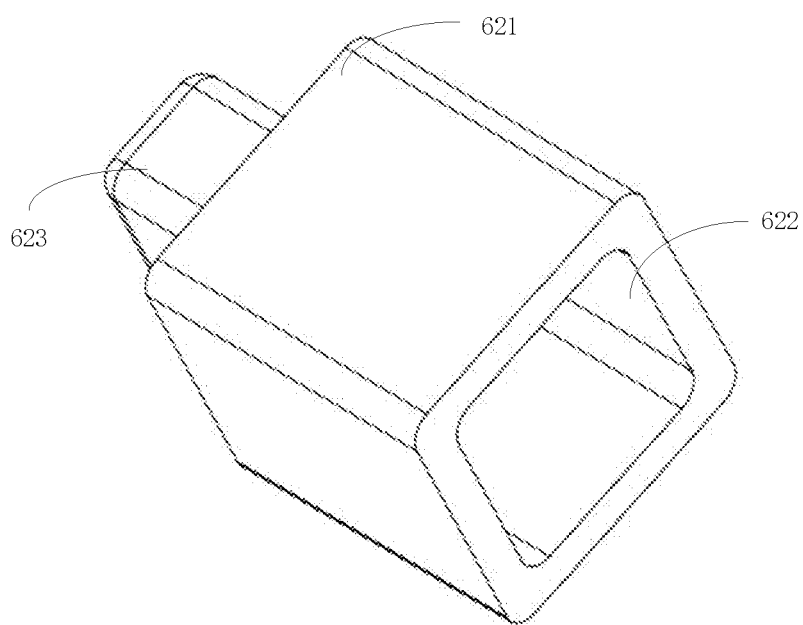
FIG. 12 is an isometric view of a second push pin in the electronic cigarette according to an embodiment of the present disclosure.

Referring to FIG. 12, the second push pin 62 has a second base 621 that is parallel with the fourth sheet 3123. A second extending part 622 is extending from one side of the second base 621, a second pushing part 623 is extending from the opposite side of the second base 621. With respect to the second base 621, a distal end of the pushing part 623 is a flat plane. The second push pin 62 has a fourth axis 624 that is perpendicular to the second axis.

Understandable, the second push pin 62 itself has the same structure as the first push pin 61, therefore, they can be manufactured via one set of mold.

The second extending part 622 is received in the second storage chamber 32, the second elastic element 52 is partially received in the second extending part 622, one end of the second elastic element 52 abuts against the fifth sheet 3133, the opposite end thereof abuts against the second base 621, The pushing part 623 passes through the opening of the fourth sheet 3123 where is outside the second storage chamber 32 to abut against the connecting body 41, that is, the second push pin 62 (the second base 621) abuts against the second elastic element 52 to compress the second elastic element 52, the opposite end of the push pin 62 (the second pushing part 623) abuts against the connector 4 (the connecting body 41). The second push pin 62 (the second extending part 622) may be slidablely received in the second storage chamber 32, and slide along an axial direction of the second storage chamber 32.

Understandable, in some embodiments, the second elastic element 52 and the second push pin 62 are connected via bezel setting.

First electrodes 71 are two, made by electrically conductive materials. The two first electrodes 71 are sleeved on the two first connecting axles 42. Each first connecting axle 42 is rotatable around the corresponding first electrode 71.

Second electrodes 72 are two, made by electrically conductive materials. The two electrodes 72 are sleeved on the two second connecting axles 43. Each second connecting axle 43 is rotatable around the corresponding second electrode 72.

Transmission parts 8 are two, made by electrically conductive materials. The two transmission parts 8 are respectively located on the fifth plane 415 and the sixth plane 416 of the connecting body 41. One of the transmission parts 8 is electrically coupled with the first connecting axle 42 and the second connecting axle 43 on the fifth plane 415. The other one of the transmission parts 8 is electrically coupled with the first connecting axle 42 and the second connecting axle 43 on the sixth plane 416.

The first positive pole contacts one of two first electrodes 71. The negative pole contacts the other one in the two first electrodes 71. The second positive pole 34 contacts one of the two second electrodes 72. The second negative pole 35 contacts one of the two second electrodes 72. The first positive pole is electrically coupled with the second positive pole 34. The first negative pole is electrically coupled with the second negative pole 35 such that the power source assembly 3 is electrically coupled with the atomizer 1. When the user compresses the button to cause the electronic cigarette 100 to work. When the atomizer 1 or the power source assembly 3 is rotating relative to the connector 4, the atomizer 1 is electrically coupled with the power source assembly 3, the electric cigarette 100 is always electrically conductive with the power source assembly 3, ensuring the electronic cigarette 100 is powered on in a process of folding or rotating, which may improve an appreciation of the electronic cigarette 100.

Understandable, the first positive pole is coupled with one of first electrodes 71 via leading wires (not shown). The first negative pole is coupled with the other one of first electrodes 71 via leading wires (not shown). The second positive pole 34 is coupled with one of the second electrodes 72 via leading wires (not shown). The second negative pole 35 is coupled with the other one of second electrodes 72 via leading wires (not shown).

The first drag springs 91 are two, made by materials with a certain elasticity and rigidity. The first drag spring 91 is shaped as a reciprocating curve. One end of each second drag spring 92 is secured to the second protruding pillar 3135, the opposite end of each second drag spring 92 is secured to the second connecting axle 43.

When the atomizer 1 is rotating around the connector 4, the second drag spring 92 provides a second elastic force. The second elastic force is adapted to prevent the atomizer 1 from rotating around the connector 4, strengthening handfeel when the user is rotating the atomizer 1.

When the power source assembly 3 rotates around the connector 4, the first drag spring 91 provides a first elastic force configured for preventing the power source assembly 3 from rotating around the connector 4, which may improve handfeel when the user is rotating the atomizer 1.

Figure 13:
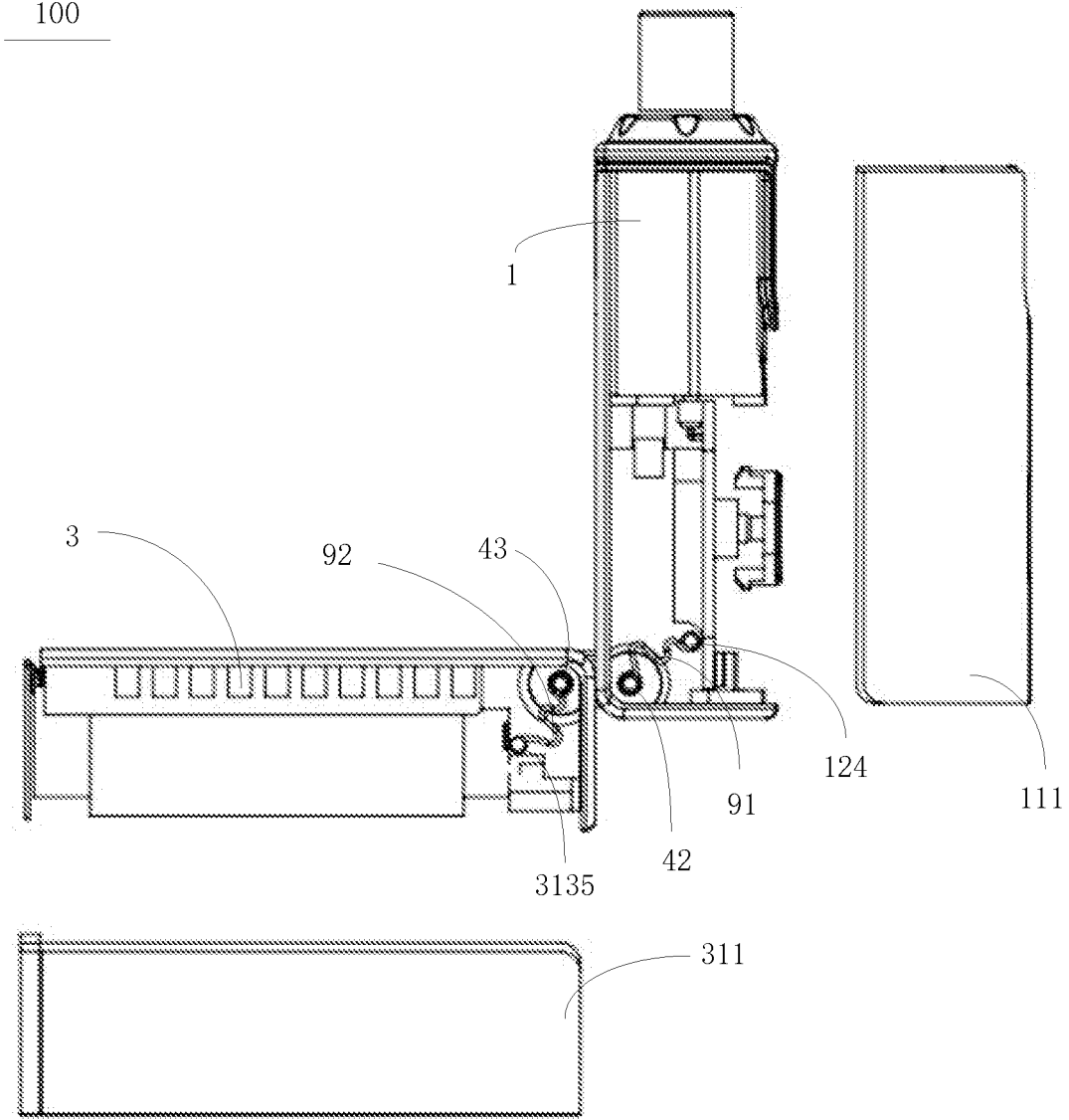
FIG. 13 is an exploded view of the electronic cigarette when a first axis is perpendicular to a second axis thereof according to an embodiment of the present disclosure.

Referring to FIG. 13, when the user is rotating the atomizer 1, since the outer diameter of the first connecting axle 42 is less than an inner diameter of the first pivot hole 123, the atomizer 1 will carry the first pivot axle 42 to move downwards while driving the first connecting axle 42 to rotate clockwise, accordingly driving the second connecting axle 43 to move upwards and enlarging a distance between the second connecting axle 43 and the second protruding pillar 3135. Then the second drag spring 92 is stretched, the second drag spring 92 gives a second elastic force to the second connecting axle 43. A direction of the second elastic force is from the second connecting axle 43 to the second protruding pillar 3135, which may cause the connector 4 to rotate anticlockwise, and prevent the connector 4 from rotating clockwise, further prevent the atomizer 1 from rotating clockwise.

When the user is rotating the atomizer 1 anticlockwise, since the outer diameter of the first connecting axle 42 is less than the inner diameter of the first pivot hole 123, the atomizer 1 will drive the first connecting axle 42 to move upwards and drive the connector 4 to rotate clockwise, thus enabling the second connecting axle 43 to move downwards, therefore a distance between the second connecting axle 43 and the second protruding pillar 3135 is diminishing, while the second drag spring 92 is compressed to give a second elastic force to the second connecting axle 43, as described herein, the second elastic force is from the second protruding pillar 3135 to the second connecting axle 43. The second elastic force drives the connector 4 to a trend of rotating clockwise, preventing the connector 4 from rotating anticlockwise, further preventing the atomizer 1 from rotating anticlockwise.

When the user rotates the power source assembly 3 clockwise, since an outer diameter of the second connecting axle 43 is less than an inner diameter of the second pivot hole 3134, the power source assembly 3 drives the second connecting axle 43 to move upwardly and drives the connector 4 to rotate clockwise, thus the first connecting axle 42 moves downwardly to enlarge the distance between the first connecting axle 42 and the first protruding pillar 124, resulting in the first drag spring 91 is stretched to give a first elastic force on the first connecting axle 42, as described herein, a direction of the first elastic force is from the first connecting axle 42 to the first protruding pillar 124. The first elastic force enables the connector 4 to rotate anticlockwise, and prevents the connector 4 from rotating clockwise, with consequently preventing the power source 3 from rotating clockwise.

When the user rotates the power source assembly 3 anticlockwise, since the outer diameter of the second connecting axle 43 is less than the inner diameter of the second pivot hole 3134, the power source assembly 3 drives the second connecting axle 43 to move downwardly and drives the connector 4 to rotate anticlockwise, thus the first connecting axle 42 moves upwardly to decrease the distance between the first connecting axle 42 and the first protruding pillar 124, resulting in the first drag spring 91 is compressed to give a first elastic force on the first connecting axle 42, as described herein, a direction of the first elastic force is from the first protruding pillar 124 to the first connecting axle 42. The first elastic force enables the connector 4 to rotate clockwise, and prevents the connector 4 from rotating anticlockwise, with consequently preventing the power source 3 from rotating anticlockwise.

In summary, when the atomizer 1 is rotating with respect to the connector 4, the second drag spring 92 exerts a second elastic force for preventing the atomizer 1 from rotating with respect to the connector 4, with consequently improving handfeel of the user rotating the atomizer 1.

When the power source assembly 3 is rotating with respect to the connector 4, the first drag spring 91 exerts a first elastic force, the first elastic force is adapted for preventing the power source assembly 3 from rotating with respect to the connector 4, with consequently improving handfeel when the user rotates the power source assembly 3.

In a process of assembling the electronic cigarette 100, the first connecting axle 42 and the second connecting axle 43 are secured to the connecting body 41, so the assembly for the connector 4 is finished.

The first magnet 21 is secured to the first substrate plate 1121 and the third magnet 23 is secured to the first plate 1123. And the second magnet 22 is secured to the second substrate plate 3121; the fourth magnet 24 is secured to the second plate 3124; then the first elastic element 51 and the first push pin 61 are secured in the first storage chamber 13, and the cover 12 is secured to the second plate 3124, afterwards assembling the circuit board assembly 14 and securing the circuit board 141 to the cover 12; next electrically coupling the heater 17 to the circuit board 141; and securing the reservoir 16 to the first plate 1123; afterwards pivotally connecting the connector 4 to the cover 12; respectively securing two ends of the first drag spring 91 to the first protruding pillar 124 and the first connecting axle 42; snapping the first shell 111 and the second shell 112 to finish the assembling of the atomizer 1.

Continue to secure the second magnet 22 to the second substrate plate 3121, and secure the fourth magnet 24 to the second plate 3124; then secure the second elastic element 52 and the second push pin 62 into the second storage chamber 32 and secure the battery 33 to the power source bezel 313; next pivotally connect the connector 4 to the power source bezel 313, and respectively secure two ends of the second drag spring 92 to the second protruding pillar 3135 and the second connecting axle 43, eventually snap the third shell 311 and the fourth shell 312 together. All in all, the assembly of the electronic cigarette 100 is finished.

Understandable, the particular processing orders or sequences as described above are not sole, which may be adjusted or changed according to different situations.

Figure 14:
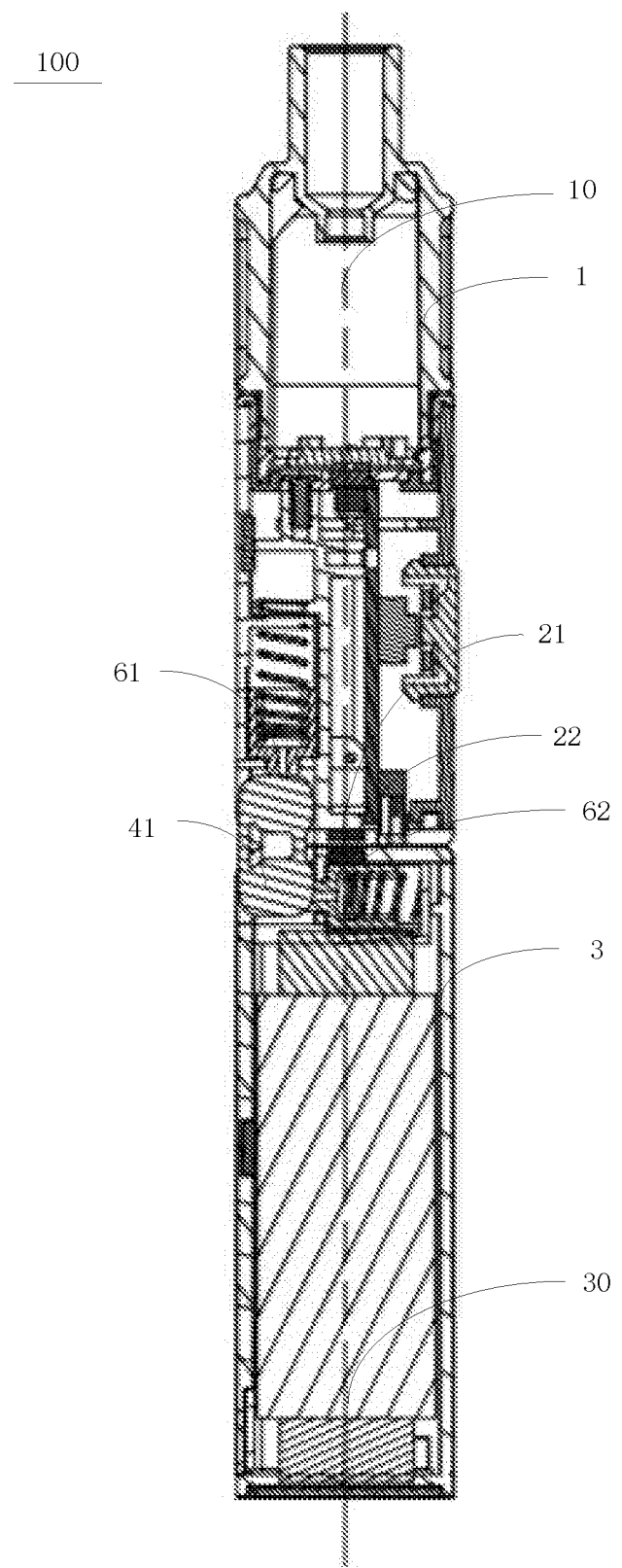
FIG. 14 is a cross-sectional view of the electronic cigarette when the first axis is coaxial with a second axis.
Figure 15:
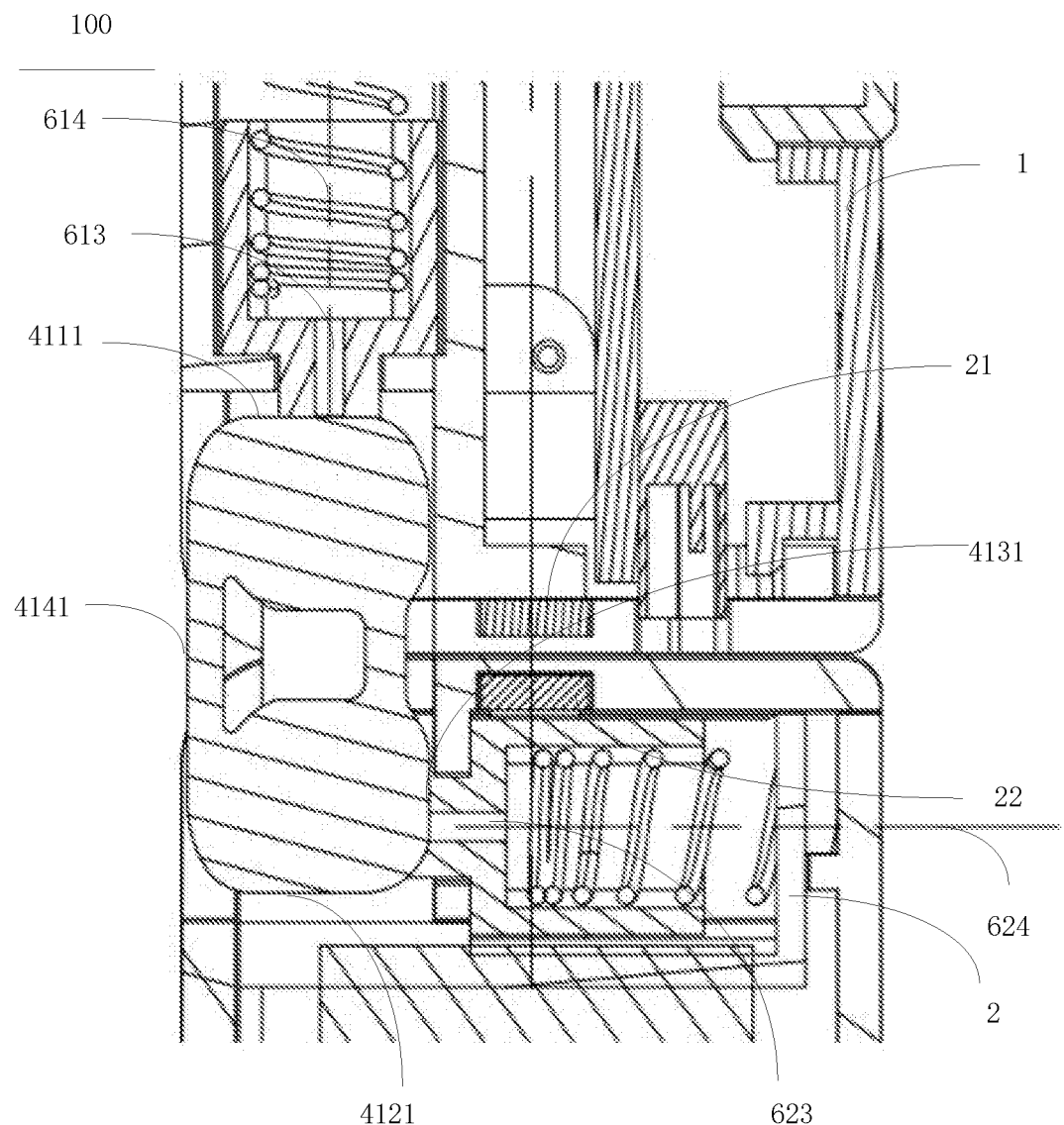
FIG. 15 is a partial enlarged view of FIG. 14.

Referring to FIGS. 14 and 15, the electronic cigarette 100 has a longest length in this case. The first axis 10 of the atomizer 1 and the second axis 30 of the power source assembly 3 are coaxial. The first pushing part 613 of the first push pin 61 abuts against the first plane 4111 of the connecting body 41. The second pushing part 623 of the second push pin 62 abuts against the third plane 4131 of the connecting body 41. The first pushing part 613 having a flat end surface allows better lamination of the first pushing part 613 and the first plane 411, which enables the electronic cigarette 100 in a more stable state, not easy to rotate, when the first axis 10 and the second axis 30 are coaxial.

In this circumstance, the first magnetic element 21 and the second magnetic element 22 are right facing with each other. And opposite surfaces of the first magnetic element 21 and the second magnetic element 22 have different magnetic polarities, so an absorption force is formed between the first magnetic element 21 and the second magnetic element 22, which enables the electronic cigarette 100 in a more stable state when the first axis 10 and the second axis 30 are coaxial.

In these circumstances, the first drag spring 91 and the second drag spring 92 are in an initial state.

Figure 16:
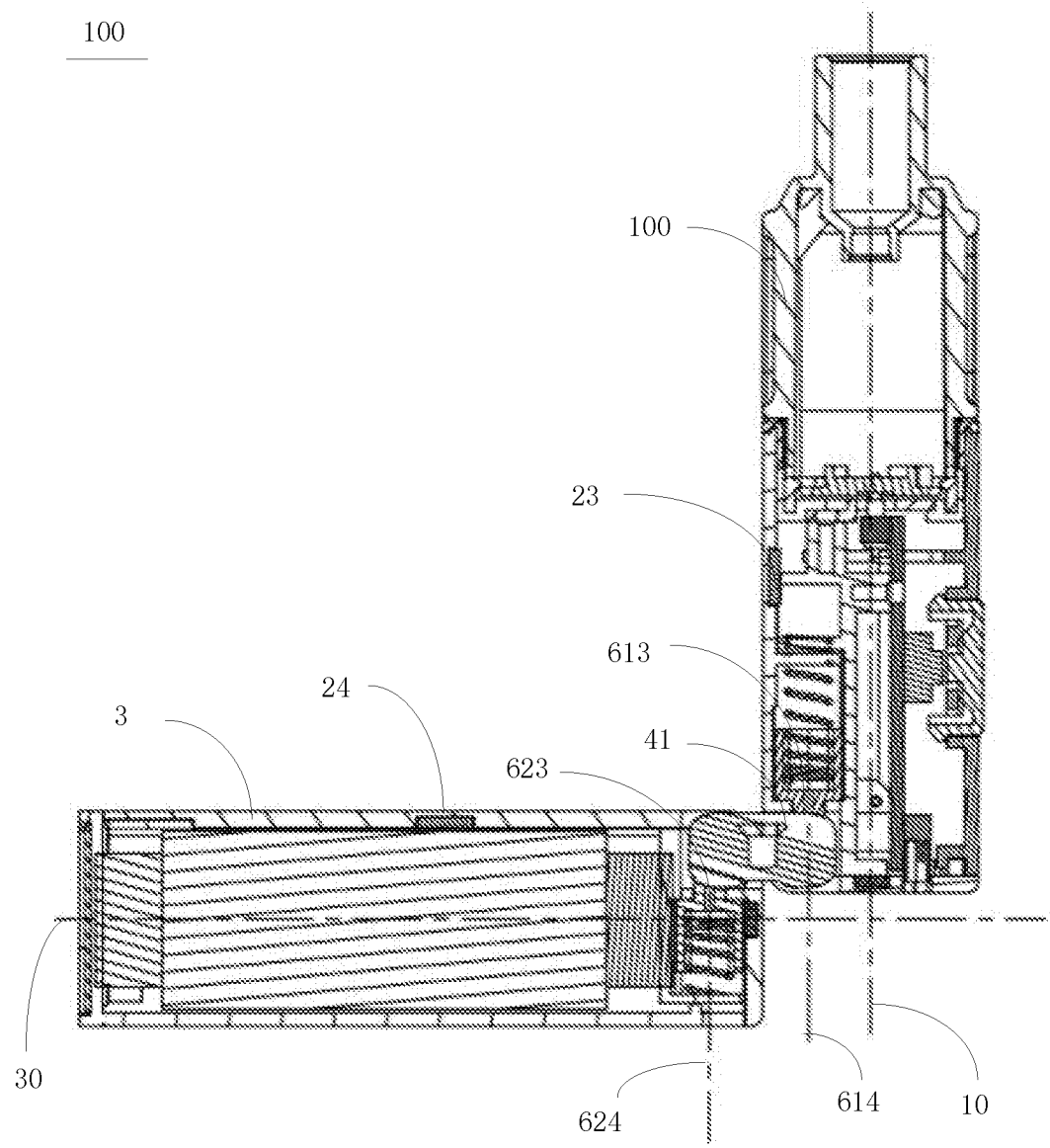
FIG. 16 is a cross-sectional view of the electronic cigarette when the first axis is perpendicular to the second axis thereof according to an embodiment of the present disclosure.
Figure 17:
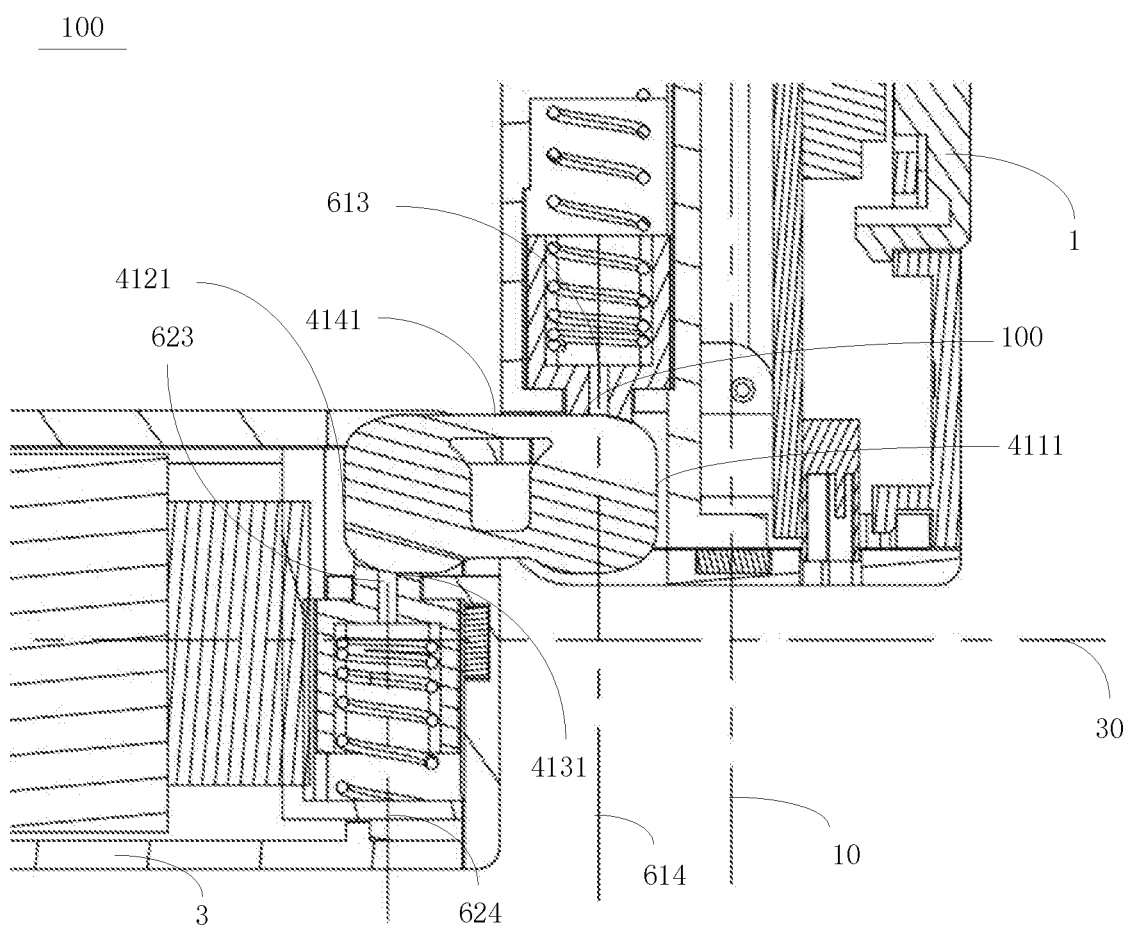
FIG. 17 is a partial enlarged view of FIG. 16.

Referring to FIGS. 16 and 17, when the first axis 10 of the atomizer 1 is perpendicular to the second axis 30 of the power source assembly 3, the first pushing part 613 of the first push pin 61 abuts against the fourth plane 4141 of the connecting body 41. The second pushing part 623 of the second push pin 62 abuts against the third plane 4131 of the connecting body 41. The first pushing part 613 has a flat end surface, allowing better lamination of the first pushing part 613 and the fourth plane 4141. The second pushing part 623 has a flat end surface, allowing better lamination of the second pushing part 623 and the third plane 4131. Therefore the electronic cigarette 100 has a stable state when the first axis 10 is perpendicular to the second axis 30.

At this moment, the first drag spring 91 and the second drag spring 92 are in the initial state.

Figure 18:
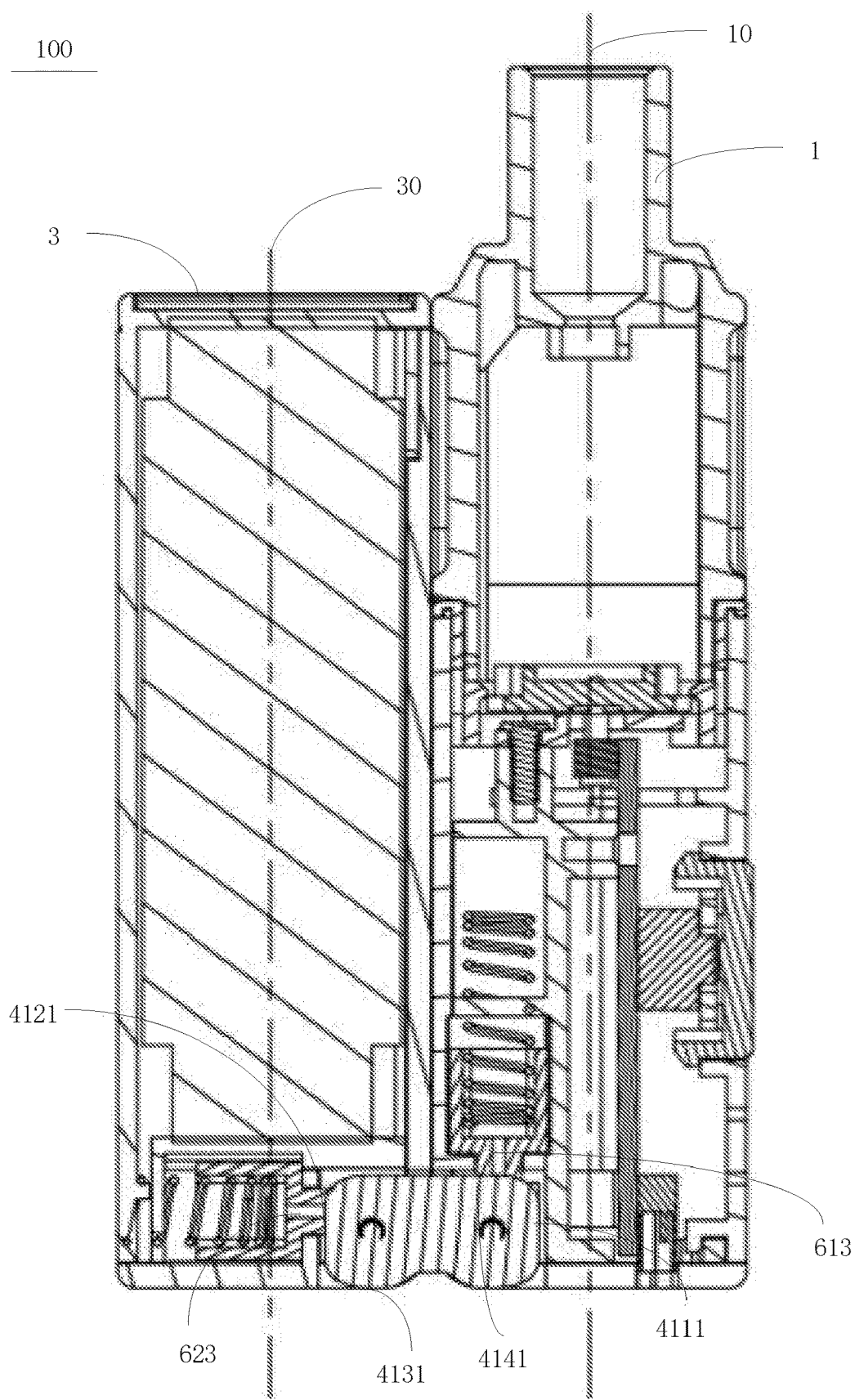
FIG. 18 is a cross-sectional view of the electronic cigarette when the first axis is parallel with the second axis thereof according to an embodiment of the present disclosure.

Referring to FIG. 18, the first axis 10 of the atomizer 1 is parallel with the second axis 30 of the power source assembly 3. The first pushing part 613 of the first push pin 61 abuts against the fourth plane 4141 of the connecting body 41. The second pushing part 623 of the second push pin 62 abuts against the second plane 4121 of the connecting body 41. The first pushing part 613 has a flat end surface, allowing better lamination of the second pushing part 623 and the second plane 4121. Therefore the electronic cigarette 100 has a more stable state, not easy to rotate when the first axis 10 is parallel with the second axis 30.

In this circumstance, the third magnetic element 23 is right facing the fourth magnetic element 24, and opposite surfaces of the third magnetic element 23 and the fourth magnetic element 24 have different magnetic polarities, so an absorption force is formed between the third magnetic element 23 and the fourth magnetic element 24, further enabling the electronic cigarette 100 in a more stable state when the first axis 10 is parallel with the second axis 30.

In this circumstance, the first drag spring 91 and the second drag spring 92 are in the initial state.

When the atomizer 1 or the power source assembly 3 is rotated, the first push pin 61 is slidable along a surface of the connector 4. The second push pin 62 is slidable along another surface of the connector 4.

In some embodiments, the atomizing shell 11 and the power source shell 31 are not to contact each other, avoiding worn or mottled around the edges of the atomizing shell 11 and the power source shell 31 when they are rubbing against each other.

Compared to the prior art, the electronic cigarette 100 provided by the present disclosure has following advantages:

1) One end of the connector 4 of the electronic cigarette 100 is pivotally connected to the atomizer 1 and the other end of the connector 4 is pivotally connected to the power source assembly 3, enabling the atomizer 1 and the power source assembly 3 to rotate with respect to the connector 4, which may realize folding of the electronic cigarette 100 to reduce the length thereof with convenience to carry it.

2) By means of the first push pin 61 and the second push pin 62 abutting against the connector 4, the process during the user is rotating the atomizer 1 or power source assembly 3 brings a better rotating experience to the user. Meanwhile, by means of the first push pin 61 and the second push pin 62 abutting against the connector 4, two propping forces are respectively supplied to the atomizer 1 and the power source assembly 3, making the atomizer 1 and the power source assembly 3 stable in a certain angle.

3) When the atomizer 1 is rotating around the connector 4, the second drag spring 92 exerts a second elastic force to prevent the atomizer 1 from rotating around the connector 4; when the power source assembly 3 is rotating around the connector 4, the first drag spring 91 exerts a first elastic force to prevent the power source assembly 3 from rotating around the connector 4, which may strength handfeel in a process that the user is rotating the electronic cigarette 100.

The illustrated methods are exemplary only. Although the methods are illustrated as having a specific operation flow, two or more operations may be combined into a single operation, a single operation may be performed in two or more separate operations, one or more of the illustrated operations may not be present in various implementations, and/or additional operations which are not illustrated may be part of the methods. In addition, the logic flows depicted in the accompanying figures and/or described herein do not necessarily require the particular order shown, or sequential order, to achieve desirable results. Other implementations may be within the scope of the following claims.

What is claimed is:

1. An electronic cigarette comprising:
   an atomizer, with a first storage chamber formed in an end thereof;
   a first elastic element, received in the first storage chamber;
   a first push pin, slidably received in the first storage chamber; the first push pin capable of sliding along an axial direction of the first storage chamber; an end of the first push pin abutting against the first elastic element;
   a power source assembly, with a second storage chamber formed in an end thereof that is closer to the atomizer;
   a second elastic element, received in the second storage chamber;
   a second push pin, slidably received in the second storage chamber; the second push pin capable of sliding along an axial direction of the second storage chamber; an end of the second push pin abutting against the second elastic element; and
   a connector, an end thereof pivotally connected to the atomizer; an opposite end thereof pivotally connected to the power source assembly;
   an opposite end of the first push pin abutting against the connector; an opposite end of the second push pin abutting against the connector; wherein when the atomizer or the power source assembly is rotating around the connector, the first push pin is capable of sliding along a surface of the connector and the second push pin is capable of sliding along another surface of the connector.

2. The electronic cigarette according to claim 1, wherein the connector comprises a connecting body, at least one first connecting axle and at least one second connecting axle, wherein the at least one first connecting axle and the at least one second connecting axle are parallel with each other, spaced apart and secured to the connecting body;
   and wherein two opposite sides of the first storage chamber are bored with first pivot holes; two opposite sides of the second storage chamber are bored with second pivot holes; the at least one first connecting axle passes through the first pivot holes; the at least one second connecting axle passes through the second pivot holes; the opposite end of the first push pin abuts against the connector; the opposite end of the second push pin abuts against the connector.

3. The electronic cigarette according to claim 2, wherein the electronic cigarette further comprises:
   a first protruding pillar carried on the atomizer;
   a second protruding pillar carried on the power source assembly;
   a first drag spring, one end thereof secured to the first protruding pillar, an opposite end thereof secured to the first connecting axle; and
   a second drag spring, one end thereof secured to the second protruding pillar, an opposite end thereof secured to the second connecting axle;
   wherein when the atomizer is rotating around the connector, the second drag spring exerts a second elastic force for preventing the atomizer from rotating around the connector; when the power source assembly is rotating around the connector, the first drag spring exerts a first elastic force for preventing the power source assembly from rotating around the connector.

4. The electronic cigarette according to claim 3, wherein the electronic cigarette further comprises:
   two first protruding pillars, respectively carried on two sides of the atomizer;
   two first drag springs, respectively carried on two sides of the atomizer;
   two second protruding pillars, respectively carried on two sides of the power source assembly; and
   two second drag springs, respectively carried on two sides of the power source assembly.

5. The electronic cigarette according to claim 3, wherein the atomizer comprises a first axis; and the power source assembly comprises a second axis;
   wherein when the first axis is coaxial with the second axis, the first drag spring and the second drag spring are in an initial state;
   when the first axis is perpendicular to the second axis, the first drag spring and the second drag spring are in an initial state;
   when the first axis is parallel with the second axis, the first drag spring and the second drag spring are in an initial state.

6. The electronic cigarette according to claim 2, wherein the connecting body comprises a first surface and a second surface opposite with each other, a third surface and a fourth surface opposite with each other, a fifth surface and a sixth surface opposite with each other; the atomizer has a first axis, the power source assembly has a second axis;
   and wherein when the first axis is coaxial with the second axis, the opposite end of the first push pin abuts against the first surface, and the opposite end of the second push pin abuts against the third surface;
   when the first axis is perpendicular to the second axis, the opposite end of the first push pin abuts against the fourth surface, and the opposite end of the second push pin abuts against the third surface;
   when the first axis is parallel with the second axis, the opposite end of the first push pin abuts against the fourth surface, and the opposite end of the second push pin abuts against the second surface.

7. The electronic cigarette according to claim 6, wherein the first push pin comprises a first base, a first extending part extending from an side of the first base and a first pushing part extending from an opposite side of the first base; and wherein the first elastic element is partially received in the first extending part to abut against the first base; the first pushing part abutting against the connector;
   the second push pin comprises a second base, a second extending part extending from an side of the second base; a second pushing part extending from an opposite side of the second base, and wherein the second elastic element is partially received in the second extending part to abut against the second base, the second pushing part abuts against the connector.

8. The electronic cigarette according to claim 7, wherein the first surface comprises a first plane, the second surface comprises a second plane, the third surface comprises a third plane, the fourth surface comprises a fourth plane, and wherein the first plane is parallel with the second plane, the third plane is parallel with the fourth plane and the third plane is perpendicular to the first plane;
wherein the first pushing part has a flat distal end with respect to the first base, and the second pushing part has a flat distal end with respect to the second base;
when the first axis and the second axis are coaxial with each other, the first pushing part abuts against the first plane, and the second push part abuts against the third plane;
when the first axis is perpendicular to the second axis, the first pushing part abuts against the fourth plane, the second pushing part abuts against the third plane;
when the first axis is parallel with the second axis, the first pushing part abuts against the fourth plane, the second pushing part abuts against the second plane.

9. The electronic cigarette according to claim 8, wherein the electronic cigarette further comprises:
a first magnetic element, secured to the atomizer; and
a second magnetic element, secured to the power source assembly;
wherein when the first axis is coaxial with the second axis, the first magnetic element right faces the second magnetic element, and wherein opposite sides of the first magnetic element and the second magnetic element have different magnetic polarities.

10. The electronic cigarette according to claim 8, wherein the electronic cigarette further comprises:
a third magnetic element, secured to the atomizer; and
a fourth magnetic element, secured to the power source assembly;
wherein when the first axis is parallel with the second axis, the third magnetic element right faces the fourth magnetic element, and wherein opposite sides of the third magnetic element and the fourth magnetic element have different magnetic polarities.

11. The electronic cigarette according to claim 8, wherein an intersection between the first plane and the fourth plane is an arc surface; an intersection between the second plane and the third plane is an arc surface.

12. The electronic cigarette according to claim 6, wherein the first push pin has a third axis, the second push pin has a fourth axis, and wherein the third axis is parallel with the first axis, the fourth axis is perpendicular to the second axis.

13. The electronic cigarette according to claim 6, wherein the electronic cigarette further comprises:
two first connecting axles coaxial with each other, and wherein an end of one first connecting axle passes through the fifth surface to be secured on the connecting body; an end of the other one first connecting axle passes through the sixth surface to be secured on the connecting body; opposite ends of the two first connecting axles respectively pass through the first pivot holes to be secured on the power source assembly;
two second connecting axles coaxial with each other, and wherein an end of one second connecting axle passes through the fifth surface to be secured on the connecting body; an end of the other one first connecting axle passes through the sixth surface to be secured on the connecting body; opposite ends of the two second connecting axles respectively pass through the second pivot holes to be secured on the power source assembly.

14. The electronic cigarette according to claim 13, wherein the electronic cigarette further comprises:
two first electrodes made by electrically conductive materials, and wherein the two first electrodes are respectively sleeved on the two first connecting axles, each first connecting axle is rotatable around the corresponding first electrode; the two first connecting axles are made by electrically conductive materials not to contact with each other;
two second electrodes made by electrically conductive materials, and wherein the two second electrodes are respectively sleeved on the two second connecting axles, each second connecting axle is rotatable around the corresponding second electrode; the two second connecting axles are made by electrically conductive materials not to contact with each other; and
two transmission parts made by electrically conductive materials, and wherein the two transmission parts are respectively located on the fifth plane and the sixth plane of the connecting body; one of the transmission parts at the fifth plane is electrically coupled with the first connecting axle and the second connecting axle; the other one of the transmission parts at the sixth plane is electrically coupled with the first connecting axle and the second connecting axle;
wherein the atomizer has a first positive contact pole and first negative pole; the first positive contact pole contacts one of the two first electrodes; the first negative pole contacts the other one of the two first electrodes; the power source assembly has a second positive pole and a second negative pole; the second positive pole contacts one of the two second electrodes, the second negative pole contacts the other one of the two second electrodes; the first positive pole is electrically coupled with the second positive pole, the first negative pole is electrically coupled with the second negative pole, so that the power source assembly is electrically coupled with the atomizer.

* * * * *

UNITED STATES PATENT AND TRADEMARK OFFICE
CERTIFICATE OF CORRECTION

| | | |
|---|---|---|
| PATENT NO. | : 11,659,862 B2 | |
| APPLICATION NO. | : 16/455802 | |
| DATED | : May 30, 2023 | |
| INVENTOR(S) | : Yifei Wu et al. | |

It is certified that error appears in the above-identified patent and that said Letters Patent is hereby corrected as shown below:

On the Title Page

Item (30) Foreign Application Priority Data should read:
--Jun 29, 2018 (CN)................................201810700964.5
Jun 29, 2018 (CN)................................201821030086.2--.

Signed and Sealed this
Fifteenth Day of August, 2023

Katherine Kelly Vidal
*Director of the United States Patent and Trademark Office*